(12) United States Patent
Li et al.

(10) Patent No.: US 11,034,986 B1
(45) Date of Patent: Jun. 15, 2021

(54) COMAMONAS TESTOSTERONI STRAIN AND USE THEREOF FOR THE SYNTHESIS OF 5-HYDROXYMETHYL-2-FURANCARBOXYLIC ACID

(71) Applicant: SOUTH CHINA UNIVERSITY OF TECHNOLOGY, Guangdong (CN)

(72) Inventors: Ning Li, Guangdong (CN); Xueying Zhang, Guangdong (CN); Minhua Zong, Guangdong (CN)

(73) Assignee: South China University of Technology

( * ) Notice: Subject to any disclaimer, the term of this patent is extended or adjusted under 35 U.S.C. 154(b) by 0 days.

(21) Appl. No.: 16/634,307

(22) PCT Filed: Dec. 14, 2017

(86) PCT No.: PCT/CN2017/116126
§ 371 (c)(1),
(2) Date: Mar. 25, 2021

(87) PCT Pub. No.: WO2019/019529
PCT Pub. Date: Jan. 31, 2019

(30) Foreign Application Priority Data

Jul. 25, 2017 (CN) .......................... 201710611915.X

(51) Int. Cl.
*C12N 1/20* (2006.01)
*C12P 17/04* (2006.01)

(52) U.S. Cl.
CPC ................ *C12P 17/04* (2013.01); *C12N 1/20* (2013.01)

(58) Field of Classification Search
CPC ................................... C12N 1/20; C12P 17/04
See application file for complete search history.

(56) References Cited

U.S. PATENT DOCUMENTS

2004/0225116 A1  11/2004  Payne et al.

FOREIGN PATENT DOCUMENTS

| CN | 101302489 A | 11/2008 |
| CN | 101434929 A | 5/2009 |
| CN | 107365724 A | 11/2017 |

OTHER PUBLICATIONS

Chinese-language International Search Report and Written Opinion issued in PCT Application No. PCT/CN2017/116126 dated May 3, 2018 with English translation (twelve (12) pages).
Yichao Wu et al., "Comparative Genome Analysis Reveals Genetic Adaptation to Versatile Environmental Conditions and Importance of Biofilm Lifestyle in Comamonas Testosteroni", Appl Microbial Biotechnol, 99(8), Mar. 19, 2015 (Mar. 19, 2015).
Yi-Lung Chen et al., "Identification of Comamonas Testosteroni as an Androgen Degrader in Sewage", scientific reports, No. 6, Oct. 13, 2016 (Oct. 13, 2016).

*Primary Examiner* — Tekchand Saidha
(74) *Attorney, Agent, or Firm* — Todd A. Serbin; Nexsen Pruet, LLC

(57) ABSTRACT

The present invention provides a *Comamonas testosteroni* strain and use thereof for the synthesis of 5-hydroxymethyl-2-furancarboxylic acid, wherein the strain is *Comamonas testosteroni* SC1588, maintained in China Center for Type Culture Collection, CCTCC for short, on Oct. 13, 2016, with an accession number of CCTCC NO: M 2016562.

21 Claims, 2 Drawing Sheets

COMAMONAS TESTOSTERONI STRAIN AND USE THEREOF FOR THE SYNTHESIS OF 5-HYDROXYMETHYL-2-FURANCARBOXYLIC ACID

RELATED APPLICATIONS

This application is the U.S. national phase filing of PCT application PCT/CN2017/116126, filed on Dec. 14, 2017, which claims the benefit of priority under Article 8 PCT of Chinese Patent Application No. 201710611915.X filed Jul. 25, 2017, the contents of which are incorporated by reference herein in their entireties.

TECHNICAL FIELD

The present invention relates to the field of biocatalysis and chemical engineering, and particularly involves a *Comamonas testosteroni* strain and use thereof for the synthesis of 5-hydroxymethyl-2-furancarboxylic acid by catalyzing the selective oxidation of 5-hydroxymethylfurfural.

BACKGROUND OF THE INVENTION

In recent years, due to the depletion of fossil resources and increasing concerns on environmental pollution, the production of bio-based fuels and platform chemicals from renewable biomass has attracted wide attention.

5-Hydroxymethylfurfural (HMF) is listed by the U. S. Department of Energy as one of the "Top 10+4" platform chemicals (Green Chem., 2010, 12, 539), and this bio-based platform chemical can be prepared via dehydration of carbohydrates. HMF has multiple reactive groups such as hydroxyl and formyl groups and carbon-carbon double bonds, and thus is readily converted into various useful intermediates. For example, HMF can be selectively oxidized to 2,5-diformylfuran (DFF), 5-hydroxymethyl-2-furancarboxylic acid (HMFCA), 5-formyl-2-furancarboxylic acid (FFCA) and 2,5-furandicarboxylic acid (FDCA), the structures of which are shown in FIG. 1. These oxidized derivatives are important building blocks and have wide applications in the energy, pharmaceutical, and polymer industries (Green Chem., 2015, 17, 3718). For example, HMFCA can be used to produce a variety of bio-based polyester materials (Makromol. Chem., 1984, 185, 2347) and is also a starting material for the synthesis of an interleukin inhibitor (J. Am. Chem. Soc., 2003, 125, 3714). Furthermore, it was found that HMFCA had an antitumor activity (Agric. Biol. Chem., 1981, 45, 2149).

Currently, HMFCA is mainly synthesized via chemical routes. Kang and Subbiah prepared HMFCA and 2,5-dihydroxymethylfuran from HMF via Cannizzaro reaction. However, the major disadvantage of this method is that, in addition to the oxidation product HMFCA, equivalent reduction product 2,5-dihydroxymethylfuran is also formed, resulting in a theoretical selectivity of only 50% (J. Ind. Eng. Chem., 2012, 18, 174; Green Chem., 2013, 15, 2849). Noble metals (e.g., platinum and gold) supported on inert carriers are widely used as catalysts for the synthesis of HMFCA (J. Mol. Catal. A: Chem., 2014, 388-389, 123; Catal. Today, 2011, 160, 55; ChemSusChem, 2009, 2, 1138). Zhang et al. reported that molybdenum dioxide acetylacetonate can efficiently catalyze the oxidation of HMF to HMFCA, and the yield of the target product is 87% after 3 h (Green Chem., 2014, 16, 2762).

DETAILED DESCRIPTION OF EMBODIMENTS OF THE INVENTION

Technical Problem

Figure 1:
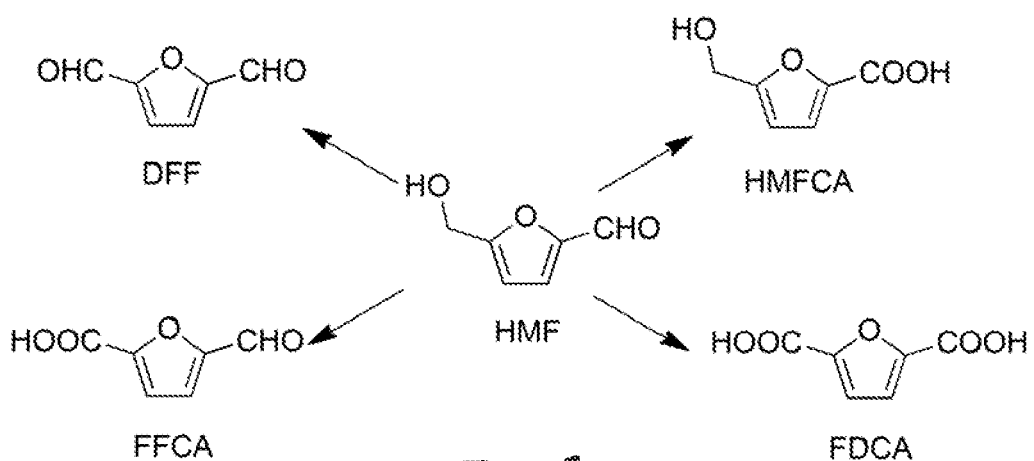
FIG. 1 shows the structures of HMF and its oxidation products.

Significant advances in chemically catalytic synthesis of HMFCA has been achieved; however, in chemical methods, heavy metals are usually used as catalysts, and the reactions are carried out in strong alkaline aqueous solutions or organic solvents such as toluene, which are environmentally unfriendly. In addition, the chemical reactions are usually conducted under harsh conditions (high temperature, high oxygen pressure conditions). The selectivities of some chemical catalysts are not satisfactory, which easily leads to further conversion of active hydroxyl groups and carboxyl groups in the product, so that the accumulation of the target product cannot be achieved. Compared to chemical counterparts, biocatalytic routes have many advantages, such as mild reaction conditions, high selectivity, being simple, and no need for environmentally unfriendly solvents and catalysts, and green process, which are of great significance to the sustainable development of society and economy. However, biocatalytic selective oxidation of I-IMF to HMFCA is still challenging because few biocatalysts are capable of catalyzing the synthesis of HMFCA. Krystof et al. synthesized HMFCA by using $H_2O_2$ as an oxidant and using lipase to catalyze the oxidation of HMF in an ethyl acetate-tert-butanol system, wherein the substrate conversion almost reached 100%, but the selectivity was not good, because of the production of about 20% byproduct HMFCA acetate (ChemSusChem, 2013, 6, 826). Recently, Zong et al. reported that xanthine oxidase enabled the oxidation of HMF to HMFCA with a high selectivity (Green Chem., 2015, 17, 3718), where the yield of the target product reached 94% after 7 h. Although xanthine oxidase can efficiently catalyze selective oxidation of HMF to HMFCA at low substrate concentration (26 mM), it has very narrow substrate scope. In addition, xanthine oxidase is expensive. Therefore, there is an urgent need to develop other biocatalysts that are highly efficient, selective, and resistant to HMF. Microorganisms, which have characteristics of rapid growth, low nutrient requirements, etc. and contain abundant endogenous enzymes, are an important class of industrial biocatalysts (Biotechnol. Adv., 2009, 27, 686). However, a major problem associated with microbial HMF conversion is that HMF has a strong inhibitory effect on microorganisms, and causes damage of the cell membrane and cell wall of microbial cells and inhibition of the RNA synthesis (Bioresour. Technol., 2000, 74, 25; Biochem. J., 2002, 363, 769; Biotechnol. Bioeng., 1999, 65, 24). In conclusion, most microorganisms are generally not resistant to HMF and their HMF conversion efficiencies remain very low.

Solution to Problem

In terms of existing problems in the prior art, the present invention presents *Comamonas testosteroni* SC1588 which is highly resistant to the substrate HMF and capable of efficiently catalyzing the selective oxidation of HMF to HMFCA. The aim of the present invention is to provide a *Comamonas testosteroni* strain and a method for the synthesis of HMFCA by using the *Comamonas testosteroni* strain to catalyze the selective oxidation of HMF.

Figure 2:
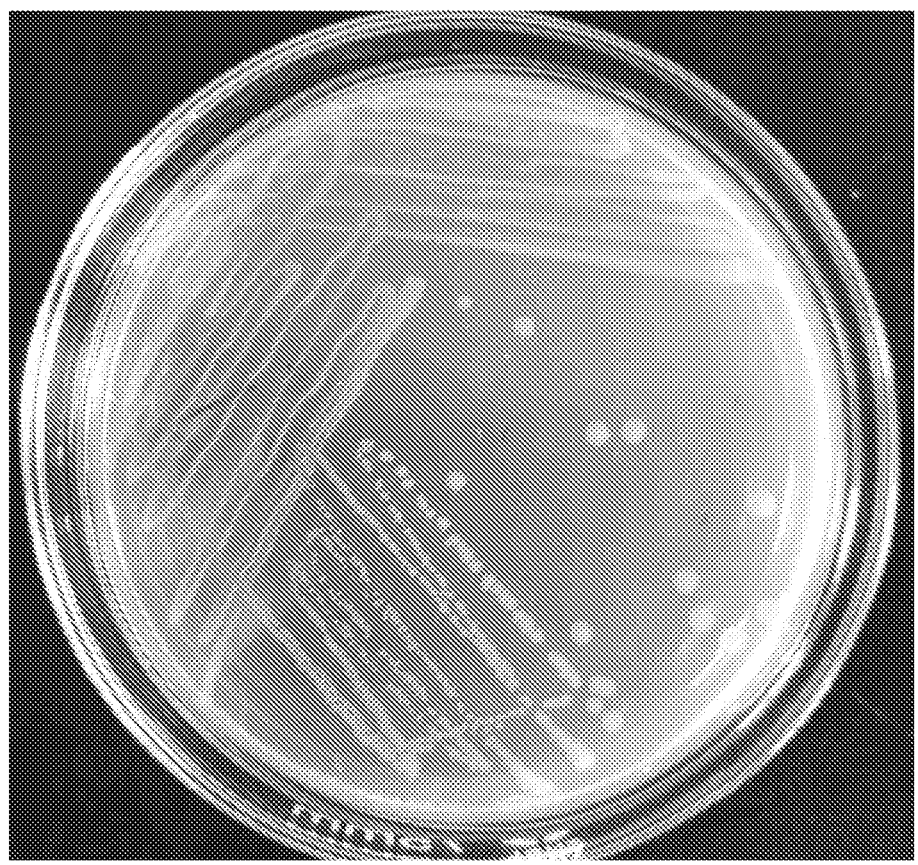
FIG. 2 shows the colony morphology of *Comamonas testosteroni* SC1588.

The aim of the invention is achieved by the following technical solution:

*Comamonas testosteroni* SC1588 is a Gram-negative, motile, strictly aerobic *bacillus*, which have milky white colonies with moist and smooth surface, and uniform texture on a nutrient broth agar plate, as shown in FIG. 2.

Use of the *Comamonas testosteroni* SC1588 for the synthesis of 5-hydroxymethyl-2-furancarboxylic acid comprises the following steps:

(1) activating and cultivating *Comamonas testosteroni* SC1588 in a nutrient broth medium, followed by harvesting the cells; and (2) adding the cells harvested in the above-mentioned step into a buffer containing 5-hydroxymethylfurfural of 10-180 mM, followed by reacting same at 10-45° C. for 8-96 hours, thereby affording 5-hydroxymethyl-2-furancarboxylic acid.

An amino acid of ≤70 mM is further added to the buffer in step (2).

The amino acid in step (2) is glycine, L-histidine, L-phenylalanine, L-alanine, L-asparagine, L-tryptophan or L-aspartate with a concentration of 20-50 mM.

The buffer in step (2) is a phosphate buffer, a Tris-HCl buffer or a glycine-NaOH buffer; and the buffer has a pH between 6.0 and 9.0.

The pH of the reaction in step (2) is controlled at 7.0-8.0.

The content of the nutrient broth medium in step (1) is 1.8%.

An inducer of 0-5 mM is added during the cultivation, wherein the inducer is furfural or furfuryl alcohol.

The cells in step (2) have a concentration of 10-30 mg/mL.

The 5-hydroxymethylfurfural in step (2) has a concentration of 40-160 mM.

The reaction in step (2) is conducted at 25-35° C. for 11-60 h with a rotational speed of 150 r/min.

Beneficial Effects of the Invention

Compared to the prior art, the present invention has the following advantages:

1) *Comamonas testosteroni* SC1588 as a catalyst can efficiently oxidize HMF with a high selectivity to the target product HMFCA, which overcomes the disadvantages of chemical catalysts that are not environmentally friendly.

2) The biocatalyst *Comamonas testosteroni* SC1588 used in the present invention has high resistance to HMF and can catalyze selective oxidation of a high concentration of substrate (160 mM) to the target product with a yield of 98%. Compared to the biocatalytic processes reported previously, the present invention allows for a higher substrate concentration, more excellent reaction efficiency, and better selectivity.

3) The process of the present invention is simple, does not require the addition of a culture medium (the addition of a culture medium makes the reaction system more complicated) and is easy to control under mild conditions, thus significantly simplifying the subsequent separation and purification process of the target product.

*Comamonas testosteroni* SC1588 of the present invention is maintained at the China Center for Type Culture Collection, CCTCC for short, on Oct. 13, 2016, with an accession number of CCTCC NO. M 2016562. Its address is Wuhan University, Wuhan, China, the deposit of which is incorporated herein by reference.

The present invention is further illustrated by embodiments, but it is not limited to those embodiments.

Embodiment 1

Activation and cultivation of *Comamonas testosteroni* SC1588: *Comamonas testosteroni* SC1588 was inoculated to 1.8% nutrient broth medium (containing 10 g/L of peptone, 3 g/L of beef extract powder and 5 g/L of sodium chloride, pH 7.2), activated at 30° C. and 150 r/min for 12 h; then the culture was added to a fresh nutrient broth medium (1.8%) at an inoculation amount of 1%, and incubated at 30° C. and 150 r/min for 5 h, followed by harvesting the cells.

Embodiment 2

Figure 3:
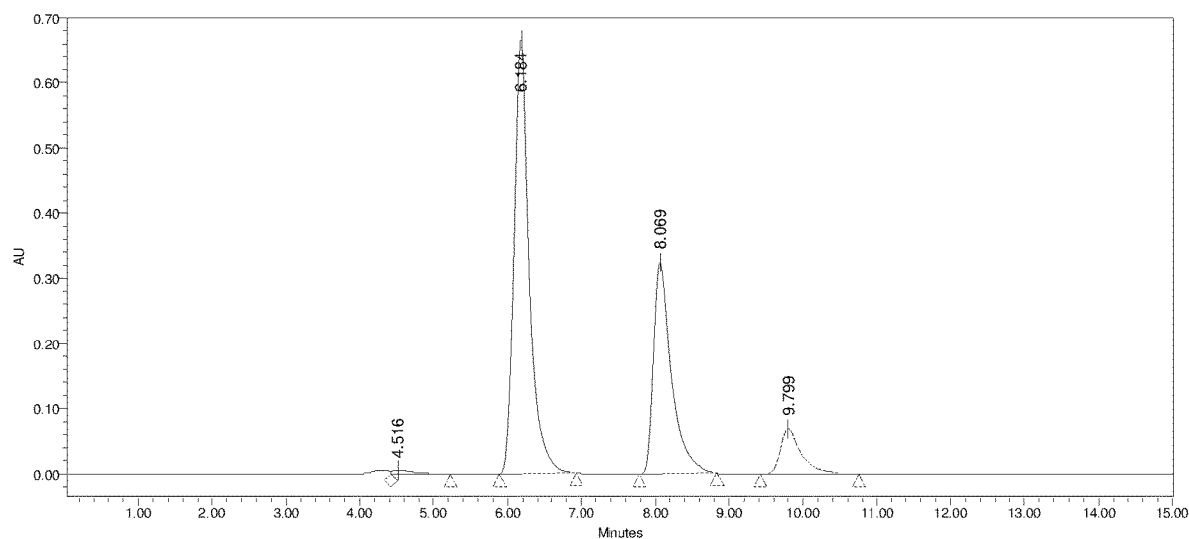
FIG. 3 shows the liquid chromatogram of HMF and HMFCA (the retention times of FDCA, HMFCA, 2,5-dihydroxymethylfuran and HMF are 4.5, 6.1, 8.1 and 9.8 min, respectively).

0.16 mmol of HMF (40 mM) was added to 4 mL of phosphate buffer (200 mM, pH 7.0) and mixed evenly; then 30 mg/mL (wet weight) of *Comamonas testosteroni* SC1588 cells activated and cultivated in embodiment 1 were added to the mixture, followed by reacting at 35° C. and 150 r/min. The reaction was monitored by liquid chromatography (FIG. 3). After 11 h, the conversion of HMF was 100% and the yield of HMFCA was 94%.

Embodiment 3

0.16 mmol of HMF (40 mM) was added to 4 mL of phosphate buffer (200 mM, pH 7.0) and mixed; then 30 mg/mL (wet weight) of *Comamonas testosteroni* SC1588 cells activated and cultivated in embodiment 1 were added to the mixture, followed by reacting at 25° C. and 150 r/min. After 11 h, the conversion of HMF was 100% and the yield of HMFCA was 91%.

Embodiment 4

0.16 mmol of HMF (40 mM) was added to 4 mL of phosphate buffer (200 mM, pH 7.0) and mixed; then 30 mg/mL (wet weight) of *Comamonas testosteroni SC*1588 cells activated and cultivated in embodiment 1 were added to the mixture, followed by reacting at 45° C. and 150 r/min. After 11 h, the conversion of HMF was 83% and the yield of HMFCA was 53%.

Embodiment 5

0.16 mmol of HMF (40 mM) was added to 4 mL of phosphate buffer (200 mM, pH 6.0) and mixed; then 30 mg/mL (wet weight) of *Comamonas testosteroni* SC1588 cells activated and cultivated in embodiment 1 were added to the mixture, followed by reacting at 30° C. and 150 r/min. After 11 h, the conversion of HMF was 100% and the yield of HMFCA was 79%.

Embodiment 6

0.16 mmol of HMF (40 mM) was added to 4 mL of phosphate buffer (200 mM, pH 8.0) and mixed; then 30 mg/mL (wet weight) of *Comamonas testosteroni* SC1588 cells activated and cultivated in embodiment 1 were added to the mixture, followed by reacting at 30° C. and 150 r/min. After 11 h, the conversion of HMF was 100% and the yield of HMFCA was 92%.

Embodiment 7

0.16 mmol of HMF (40 mM) was added to 4 mL of Tris-HCl buffer (50 mM, pH 9.0) and mixed; then 30 mg/mL (wet weight) of *Comamonas testosteroni* SC1588 cells activated and cultivated in embodiment 1 were added to the mixture, followed by reacting at 30° C. and 150 r/min. After 24 h, the conversion of HMF was 99% and the yield of HMFCA was 82%.

Embodiment 8

0.44 mmol of HMF (110 mM) was added to 4 mL of phosphate buffer (200 mM, pH 7.0) and mixed; then 30 mg/mL (wet weight) of *Comamonas testosteroni* SC1588 cells activated and cultivated in embodiment 1 were added to the mixture, followed by reacting at 30° C. and 150 r/min. After 48 h, the conversion of HMF was 100% and the yield of HMFCA was 96%.

Embodiment 9

0.52 mmol of HMF (130 mM) was added to 4 mL of phosphate buffer (200 mM, pH 7.0) and mixed; then 30 mg/mL (wet weight) of *Comamonas testosteroni* SC1588 cells activated and cultivated in embodiment 1 were added to the mixture, followed by reacting at 30° C. and 150 r/min. After 60 h, the conversion of HMF was 100% and the yield of HMFCA was 82%.

Embodiment 10

0.52 mmol of HMF (130 mM) and 0.08 mmol of histidine (20 mM) were added to 4 mL of phosphate buffer (200 mM, pH 7.0) and mixed; then 30 mg/mL (wet weight) of *Comamonas testosteroni* SC1588 cells activated and cultivated in embodiment 1 were added to the mixture, followed by reacting at 30° C. and 150 r/min. After 60 h, the conversion of HMF was 100% and the yield of HMFCA was 91%.

Embodiment 11

0.52 mmol of HMF (130 mM) and 0.08 mmol of glycine (20 mM) were added to 4 mL of phosphate buffer (200 mM, pH 7.0) and mixed; then 30 mg/mL (wet weight) of *Comamonas testosteroni* SC1588 cells activated and cultivated in embodiment 1 were added to the mixture, followed by reacting at 30° C. and 150 r/min. After 48 h, the conversion of HMF was 100% and the yield of HMFCA was 86%.

Embodiment 12

0.52 mmol of HMF (130 mM) and 0.08 mmol of L-alanine (20 mM) were added to 4 mL of phosphate buffer (200 mM, pH 7.0) and mixed; then 30 mg/mL (wet weight) of *Comamonas testosteroni* SC1588 cells activated and cultivated in embodiment 1 were added to the mixture, followed by reacting at 30° C. and 150 r/min. After 48 h, the conversion of HMF was 100% and the yield of HMFCA was 88%.

Embodiment 13

0.52 mmol of HMF (130 mM) was added to 4 mL of phosphate buffer (200 mM, pH 7.0) and mixed; then 30 mg/mL (wet weight) of *Comamonas testosteroni* SC1588 cells activated and cultivated in embodiment 1 were added to the mixture, and incubated at 30° C. and 150 r/min for 24 h; then the pH of the reaction system was adjusted to 7.0 by the addition of sodium bicarbonate. After 54 h, the conversion of HMF was 100% and the yield of HMFCA was 94%.

Embodiment 14

0.64 mmol of HMF (160 mM) and 0.08 mmol of histidine (20 mM) were added to 4 mL of phosphate buffer (200 mM, pH 7.0) and mixed; then 30 mg/mL (wet weight) of *Comamonas testosteroni* SC1588 cells activated and cultivated in embodiment 1 were added to the mixture, followed by reacting at 30° C. and 150 r/min. During the reaction, the pH of the reaction system was adjusted to 7.0 by the addition of sodium bicarbonate every 24 h. After 60 h, the conversion of HMF was 100% and the yield of HMFCA was 92%.

Embodiment 15

0.72 mmol of HMF (180 mM) and 0.08 mmol of histidine (20 mM) were added to 4 mL of phosphate buffer (200 mM, pH 7.0) and mixed; then 30 mg/mL (wet weight) of *Comamonas testosteroni* SC1588 cells activated and cultivated in embodiment 1 were added to the mixture, followed by reacting at 30° C. and 150 r/min. During the reaction, the pH of the reaction system was adjusted to 7.0 by the addition of sodium bicarbonate every 24 h. After 96 h, the conversion of HMF was 100% and the yield of HMFCA was 46%.

Embodiment 16

0.6 mmol of HMF (150 mM) was added to 4 mL of phosphate buffer (200 mM, pH 7.0) and mixed; then 30 mg/mL (wet weight) of *Comamonas testosteroni* SC1588 cells activated and cultivated in embodiment 1 were added to the mixture, followed by reacting at 30° C. and 150 r/min. After 60 h, the conversion of HMF was 100% and the yield of HMFCA was 76%.

Embodiment 17

*Comamonas testosteroni* SC1588 was inoculated to 1.8% nutrient broth medium and cultivated at 30° C. and 150 r/min for 12 h; then the culture was added to a fresh nutrient broth medium (1.8%) containing 5 mM of furfuryl alcohol at an inoculation amount of 1%, and cultivated at 30° C. and 150 r/min for 5 h, followed by harvesting the cells.

0.6 mmol of HMF (150 mM) was added to 4 mL of phosphate buffer (200 mM, pH 7.0) and mixed; then 30 mg/mL (wet weight) of *Comamonas testosteroni* SC1588 cells activated and cultivated above were added to the mixture, followed by reacting at 30° C. and 150 r/min. After 36 h, the conversion of HMF was 100% and the yield of HMFCA was 76%.

Embodiment 18

*Comamonas testosteroni* SC1588 was inoculated to 1.8% nutrient broth medium and cultivated at 30° C. and 150 r/min for 12 h; then the culture was added to a fresh nutrient broth medium (1.8%) containing 5 mM of furfural at an inoculation amount of 1%, and cultivated at 30° C. and 150 r/min for 5 h, followed by harvesting the cells.

0.6 mmol of HMF (150 mM) was added to 4 mL of phosphate buffer (200 mM, pH 7.0) and mixed; then 30 mg/mL (wet weight) of *Comamonas testosteroni* SC1588 cells activated and cultivated above were added to the mixture, followed by reacting at 30° C. and 150 r/min. After 36 h, the conversion of HMF was 100% and the yield of HMFCA was 75%.

Embodiment 19

*Comamonas testosteroni* SC1588 was inoculated to 1.8% nutrient broth medium and cultivated at 30° C. and 150 r/min for 12 h; then the culture was added to a fresh nutrient broth medium (1.8%) containing 5 mM of furfuryl alcohol at an inoculation amount of 1%, and cultivated at 30° C. and 150 r/min for 5 h, followed by harvesting the cells.

8 mmol of HMF (160 mM) and 1 mmol of histidine (20 mM) were added to 50 mL of phosphate buffer (200 mM, pH 7.0) and mixed; then 30 mg/mL (wet weight) of *Comamonas testosteroni* SC1588 cells activated and cultivated above were added to the mixture, followed by reacting at 30° C. and 150 r/min. After the reaction of 24 h, the pH of the reaction system was adjusted to 7.0 by the addition of sodium bicarbonate. After 36 h, the conversion of HMF was 100% and the yield of HMFCA was 98%.

Control Embodiment 1

0.16 mmol of HMF (40 mM) and 0.9% of nutrient broth were added to 4 mL of phosphate buffer (200 mM, pH 7.0) and mixed; then 30 mg/mL (wet weight) of *Comamonas testosteroni* SC1588 cells activated and cultivated in embodiment 1 were added to the mixture, followed by reacting at 35° C. and 150 r/min. After 11 h, the conversion of HMF was 100% and the yield of HMFCA was 73%.

Control Embodiment 2

0.16 mmol of HMF (40 mM) and 0.32 mmol of acetone were added to 4 mL of phosphate buffer (200 mM, pH 7.0) and mixed; then 30 mg/mL (wet weight) of *Comamonas testosteroni* SC1588 cells activated and cultivated in embodiment 1 were added to the mixture, followed by reacting at 35° C. and 150 r/min. After 11 h, the conversion of HMF was 100% and the yield of HMFCA was 81%.

The invention claimed is:

1. A method synthesizing of 5-hydroxymethyl-2-furancarboxylic acid by contacting the *Comamonas testosteroni* SC1588 strain, maintained in China Center for Type Culture Collection, CCTCC for short, on Oct. 13, 2016, with an accession number of CCTCC NO: M 2016562, with 5-hydroxymethyl furfural.

2. The method according to claim 1, characterized by comprising:
   (1) activating and cultivating *Comamonas testosteroni* SC1588 in a nutrient broth medium, followed by harvesting the cells; and
   (2) adding the cells harvested in the above-mentioned step into a buffer containing 5-hydroxymethylfurfural of 10-180 mM, followed by reacting the same at 10-45° C. for 8-96 hours, thereby affording 5-hydroxymethyl-2-furancarboxylic acid.

3. The method according to claim 2, characterized in that, an amino acid of ≤70 mM is further added to the buffer in step (2).

4. The method according to claim 3, characterized in that, the amino acid in step (2) is glycine, L-histidine, L-phenylalanine, L-alanine, L-asparagine, L-tryptophan or L-aspartate with a concentration of 20-50 mM.

5. The method according to claim 4, characterized in that, the buffer in step (2) is a phosphate buffer, a Tris-HCl buffer or a glycine-NaOH buffer; and the buffer has a pH between 6.0 and 9.0.

6. The method according to claim 5, characterized in that, the pH of the reaction in step (2) is controlled at 7.0-8.0.

7. The method according to claim 2, characterized in that, the content of the nutrient broth medium in step (1) is 1.8%, and an inducer of 0-5 mM is added during the cultivation, wherein the inducer is furfural or furfuryl alcohol.

8. The method according to claim 2, characterized in that, the cells in step (2) have a concentration of 10-30 mg/mL, and the 5-hydroxymethylfurfural has a concentration of 40-160 mM.

9. The method according to claim 8, characterized in that, the reaction in step (2) is conducted at 25-35° C. for 11-60 h with a rotational speed of 150 r/min.

10. The method according to claim 3, characterized in that, the content of the nutrient broth medium in step (1) is 1.8%, and an inducer of 0-5 mM is added during the cultivation, wherein the inducer is furfural or furfuryl alcohol.

11. The method according to claim 4, characterized in that, the content of the nutrient broth medium in step (1) is 1.8%, and an inducer of 0-5 mM is added during the cultivation, wherein the inducer is furfural or furfuryl alcohol.

12. The method according to claim 5, characterized in that, the content of the nutrient broth medium in step (1) is 1.8%, and an inducer of 0-5 mM is added during the cultivation, wherein the inducer is furfural or furfuryl alcohol.

13. The method according to claim 6, characterized in that, the content of the nutrient broth medium in step (1) is 1.8%, and an inducer of 0-5 mM is added during the cultivation, wherein the inducer is furfural or furfuryl alcohol.

14. The method according to claim 3, characterized in that, the cells in step (2) have a concentration of 10-30 mg/mL, and the 5-hydroxymethylfurfural has a concentration of 40-160 mM.

15. The method according to claim 4, characterized in that, the cells in step (2) have a concentration of 10-30 mg/mL, and the 5-hydroxymethylfurfural has a concentration of 40-160 mM.

16. The method according to claim 5, characterized in that, the cells in step (2) have a concentration of 10-30 mg/mL, and the 5-hydroxymethylfurfural has a concentration of 40-160 mM.

17. The according to claim 6, characterized in that, the cells in step (2) have a concentration of 10-30 mg/mL, and the 5-hydroxymethylfurfural has a concentration of 40-160 mM.

18. The method according to claim 14, characterized in that, the reaction in step (2) is conducted at 25-35° C. for 11-60 h with a rotational speed of 150 r/min.

19. The method according to claim 15, characterized in that, the reaction in step (2) is conducted at 25-35° C. for 11-60 h with a rotational speed of 150 r/min.

20. The method according to claim 16, characterized in that, the reaction in step (2) is conducted at 25-35° C. for 11-60 h with a rotational speed of 150 r/min.

21. The method according to claim 17, characterized in that, the reaction in step (2) is conducted at 25-35° C. for 11-60 h with a rotational speed of 150 r/min.

* * * * *